US008766027B1

(12) United States Patent
Subramaniyam

(10) Patent No.: US 8,766,027 B1
(45) Date of Patent: Jul. 1, 2014

(54) ADDITIVE COMPOSITION FOR CONTROL AND INHIBITION OF POLYMERIZATION OF STYRENE, AND METHOD OF PREPARATION AND USE THEREOF

(75) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 0 days.

(21) Appl. No.: 14/240,817

(22) PCT Filed: Aug. 17, 2012

(86) PCT No.: PCT/IN2012/000553
§ 371 (c)(1),
(2), (4) Date: Feb. 25, 2014

(87) PCT Pub. No.: WO2013/054353
PCT Pub. Date: Apr. 18, 2013

(30) Foreign Application Priority Data

Aug. 26, 2011 (IN) .......................... 2403/MUM/2011

(51) Int. Cl.
| | |
|---|---|
| *C08F 2/40* | (2006.01) |
| *C08F 12/08* | (2006.01) |
| *C07C 7/20* | (2006.01) |
| *C07C 15/46* | (2006.01) |
| *C09K 15/24* | (2006.01) |

(52) U.S. Cl.
CPC ................. *C07C 15/46* (2013.01); *C09K 15/24* (2013.01)
USPC ................................ 585/428; 585/4; 585/406

(58) Field of Classification Search
CPC ............. C08F 2/40; C08F 12/08; C07C 7/20
USPC ............................................. 585/4, 428, 406
See application file for complete search history.

(56) References Cited

U.S. PATENT DOCUMENTS

| | | |
|---|---|---|
| 6,342,648 B1 | 1/2002 | Shahid |
| 7,651,635 B1 | 1/2010 | Lewis |
| 2004/0034247 A1 | 2/2004 | Eldin |
| 2006/0020089 A1 | 1/2006 | Merrill |

FOREIGN PATENT DOCUMENTS

| | | |
|---|---|---|
| WO | 2013054353 A1 | 4/2013 |
| WO | 2013054353 A4 | 4/2013 |

OTHER PUBLICATIONS

Foreign communication from the priority application—International Search Report and Written Opinion, PCT/IN2012/000553, Mar. 6, 2013, 9 pages.
Foreign communication from the priority application—International Preliminary Report on Patentability, PCT/IN2012/000553, Oct. 7, 2013, 7 pages.

*Primary Examiner* — Thuan D Dang
(74) *Attorney, Agent, or Firm* — Conley Rose, P.C.; Rodney B. Carroll

(57) ABSTRACT

The present invention relates to additive composition for control and inhibition of polymerization of styrene, wherein the composition comprises amine and quinone methide, and wherein the amine is polymerization non-inhibitor amine. In one embodiment, the present invention relates to method of preparation and use of additive composition to control and inhibit polymerization of styrene, wherein the composition comprises amine and quinone methide, and wherein the amine is polymerization non-inhibitor amine. In another embodiment, the present invention relates to additive composition for control and inhibition of polymerization of styrene, wherein the composition comprises oxide treated derivative of amine and quinone methide, and wherein the amine is polymerization non-inhibitor amine, and to the method of preparation and use thereof.

25 Claims, No Drawings

ADDITIVE COMPOSITION FOR CONTROL AND INHIBITION OF POLYMERIZATION OF STYRENE, AND METHOD OF PREPARATION AND USE THEREOF

CROSS-REFERENCE TO RELATED APPLICATIONS

This application is a filing under 35 U.S.C. 371 of International Application No. PCT/IN2012/000553 filed Aug. 17, 2012, entitled "Additive Composition for Control and Inhibition of Polymerization of Styrene, and Method of Preparation and Use Thereof," which claims priority to Indian Patent Application No. 2403/MUM/2011 filed Aug. 26, 2011, which applications are incorporated by reference herein in their entirety.

FIELD OF THE INVENTION

The present invention relates to additive composition for control and inhibition of polymerization of monomers, particularly of styrene.

In one embodiment, the present invention relates to method of preparation of additive composition for control and inhibition of polymerization of monomers, particularly of styrene.

In another embodiment, the present invention relates to use of additive composition to control and inhibit polymerization of monomers, particularly of styrene.

BACKGROUND OF THE INVENTION

The polymerization of monomers, particularly of styrene during processing is a matter of concern, because it causes formation of unwanted polymers and results in loss of yield of end product and makes the process un-economical.

In the art use of inhibitors and retarders, and combination thereof to overcome problem of polymerization of styrene has been reported.

The problem of using the inhibitors alone is that these are to be added continuously or at regular interval, because once they are consumed, the polymerization will re-start.

The problem of using the retarders is that these are not very effective to reduce polymerization of styrene to a level of substantial inhibition or to the acceptable level of inhibition.

The prior art discloses use of quinone methide (QM) as polymerization inhibitor. However, the inventor has found [refer to examples] that main problem of using the quinone methide is that it has to be used in higher amounts to achieve acceptable level of inhibition, and such higher amount not only result in increase of cost of process, but also result in formation of undesired products due to unstable nature of quinone methide.

The prior art also proposes quinone methide based composition comprising quinone methide and 4HT (4 hydroxy tempo 2,2,6,6-tetramethyl-,1-oxide) as styrene polymerization inhibitor. However, the inventor has found [refer to examples] that main problem of using this known composition of quinone methide is that even at higher amounts the problem of polymerization is not resolved to acceptable level.

The prior art [U.S. Pat. No. 7,651,635] discloses use of combination of an inhibitor and a retarder, wherein the inhibitor is polymerization inhibitor consisting of alkylhydroxylamine and retarder is 7-substituted quinone methide. The main problem of this composition is that it employs inhibitor, which are consumed continuously and get gradually depleted, and hence, the inhibitor has to be added continuously or intermittently or at least it has to be ensured that an appropriate amount of the inhibitor is maintained in the system [Col. 4, lines 7-13 of U.S. Pat. No. '635].

The prior art D1 (US 2004/034247 A1) discloses additive composition for control and inhibition of polymerization of styrene comprising quinone methide 4-benzylidene,2,6-di-tert-butyl-cyclohexa-2,5-dienone (QM), hydroxylamine and catechol, which is 4-tert-butyl catechol (TBC) (re abstract, paragraphs [0009], [0019], [0024], Examples, Table 1, claim 1, claim 10 of D1).

The prior art D2 (US 2006/020089 A1) discloses use of phenylenediamine in combination with QM (re its Example 3, paragraph no. [0033]).

The prior art D3 (U.S. Pat. No. 6,342,648 B1) discloses oxidised amines, but it neither discloses nor suggests the combination thereof with methides.

In accordance with present invention, the "acceptable level of inhibition of polymerization of styrene" is inhibition of polymerization of at least 98.5%, preferably at least 99% of styrene, that is only up to 1.5%, especially up to 1% of styrene polymerizes.

NEED OF THE INVENTION

Therefore, there is still a need of additive composition which is not only suitable for substantial control and inhibition of polymerization of styrene, but is also required in very low dosage.

There is also a need to have a method of preparation of additive composition suitable for substantial control and inhibition of polymerization of styrene, particularly at a very low dosage.

There is further a need to have a method of use of additive composition to substantially control and inhibit polymerization of styrene, particularly at a very low dosage.

PROBLEM TO BE SOLVED BY THE INVENTION

Therefore, the present invention aims at providing a solution to above-described existing industrial problem by providing additive composition which is not only suitable for substantial control and inhibition of polymerization of styrene, but is also required in very low dosage.

The present invention also aims at providing a solution to above-described existing industrial problem by providing a method of preparation of additive composition suitable for substantial control and inhibition of polymerization of styrene, particularly at a very low dosage.

The present invention also aims at providing a solution to above-described existing industrial problem by providing a method of use of additive composition to substantially control and inhibit polymerization of styrene, particularly at a very low dosage.

OBJECTS OF THE INVENTION

Accordingly, the main object of present invention is to provide additive composition which is not only suitable for substantial control and inhibition of polymerization of styrene, but is also required in very low dosage as compared to dosage of prior art additives for achieving the same or better level of inhibition of polymerization of styrene.

Another object of present invention is to provide a method of preparation of additive composition suitable for substantial control and inhibition of polymerization of styrene, particularly at a very low dosage as compared to dosage of prior art additives for achieving the same or better level of inhibition of polymerization of styrene.

Still another object of present invention is to provide a method of use of additive composition to substantially control and inhibit polymerization of styrene, particularly at a very low dosage as compared to dosage of prior art additives for achieving the same or better level of inhibition of polymerization of styrene.

The present invention aims at providing additive composition which can give acceptable level of inhibition of polymerization, i.e. reduce the polymerization of monomer including styrene even at low active dosage as compared to dosage of prior art additives for achieving the same or better level of inhibition of polymerization of styrene.

The present invention aims at providing additive composition which is suitable to substantially reduce polymerization of monomer including styrene to less than 1.5%, especially to less than 1.0% even at low active dosage as compared to dosage of prior art additives for achieving the same or better acceptable level of inhibition of polymerization of styrene.

The present invention also aims at providing additive composition wherein amount of quinone methide is reduced in the additive composition, and therefore, the composition of present invention is economical. The quinone methide is expensive and not easily available.

Other objects and advantages of present invention will become more apparent from the following description when read in conjunction with examples, which are not intended to limit scope of present invention.

DESCRIPTION OF THE INVENTION

With aim to overcome above-described problems of prior art and to achieve above-described objects of the invention, the inventor has found that when a composition comprising polymerization non-inhibiting amine of present invention and quinone methide is employed, the polymerization of styrene is, surprisingly and unexpectedly, controlled and inhibited substantially to the acceptable level (as defined herein).

It is further surprising and unexpected that some of the polymerization non-inhibiting amines of present invention result in about nil (substantially zero percent) polymerization of styrene, that is, have been found to be capable of controlling and inhibiting the polymerization of styrene to the extent of about 100%, and some of the polymerization non-inhibiting amines of present invention result in about 1% polymerization of styrene, that is, have been found to be capable of controlling and inhibiting the polymerization of styrene to the extent of about 99%, which is substantially high control and inhibition of polymerization of styrene.

Accordingly, the present invention relates to additive composition for control and inhibition of polymerization of styrene, wherein the composition comprises amine and quinone methide, and wherein the amine is polymerization non-inhibitor amine.

The term "amine is polymerization non-inhibitor amine" means, contrary to disclosure and teachings of prior art, the amine per se is not capable of inhibiting polymerization of styrene to the acceptable level. It has been found that the polymerization non-inhibiting amines of present invention result in substantially high polymerization of about 14 to 18% polymerization of styrene as against 19.66% polymerization of styrene for blank example run without amine (see Table 2), and therefore, the "amines" of present invention are named as "polymerization non-inhibitor amines".

In accordance with one of the embodiments of the present invention the polymerization non-inhibiting amine is selected from the group comprising tri isopropanol amine (TIPA), propoxylated ethylene diamine (PED), triethanol amine (TEA), tributyl amine (TBA), diethanol amine (DEA), mono ethanol amine (MEA), and combination thereof.

In accordance with preferred embodiment of the present invention, the polymerization non-inhibiting amine is tri isopropanol amine (TIPA).

In accordance with one of the preferred embodiments of the present invention, the polymerization non-inhibiting amine is propoxylated ethylene diamine (PED).

In accordance with another preferred embodiment of the present invention, the polymerization non-inhibiting amine is tributyl amine (TBA).

In accordance with still another preferred embodiment of the present invention, the polymerization non-inhibiting amine is diethanol amine (DEA).

In accordance with yet another preferred embodiment of the present invention, the polymerization non-inhibiting amine is triethanol amine (TEA).

In accordance with further preferred embodiment of the present invention, the polymerization non-inhibiting amine is mono ethanol amine (MEA).

In accordance with one of the preferred embodiments of the present invention, the propoxylated ethylene diamine (PED) is one as available from BASF under the tradename Quadrol 204®. However, the present invention is not limited to Quadrol 204®.

The inventor has also found that when oxide treated derivative of amine is employed in present composition, the efficiency of the amine, surprisingly and unexpectedly, improves further. The inventor confirms that the oxide treated derivatives of amine includes ethylene oxide, propylene oxide and butylene oxide treated derivatives of amines.

Therefore, in one embodiment, the present invention also relates to the composition for controlling and inhibiting polymerization of styrene comprising oxide treated derivative of amine and quinone methide, wherein the amine is polymerization non-inhibitor amine.

In accordance with one of the preferred embodiments of the present invention, the oxide treated derivative of amine is selected from a group comprising ethylene oxide, propylene oxide and butylene oxide treated derivatives of amine.

In accordance with one of the preferred embodiments of the present invention, the oxide treated derivative of amine is ethoxylated (ethylene oxide treated) derivative of N,N,disec-butyl-para-phenylene diamine (UOP5+EO).

In accordance with one of the embodiments of the present invention, the composition may comprise up to about 50% of the present amine or oxide treated derivative of amine. However, it has been, surprisingly and unexpectedly, found that when percent amount of present amine or oxide treated derivative of amine is increased beyond about 15%, especially beyond about 10%, the efficiency of the composition comprising present amine or oxide treated derivative of amine starts decreasing with increase in percent amount of the present amine or oxide treated derivative of amine. However, it still gives desired acceptable efficiency at slightly higher dosage, for example, at the dosage of about 300 ppm.

Therefore, in accordance with one of the embodiments of the present invention, the quinone methide and polymerization non-inhibiting amine or oxide treated derivative of amine of the present composition are taken in percent ratio varying from about 99:1 and about 50:50.

However, in accordance with one of the preferred embodiments of the present invention, the quinone methide and polymerization non-inhibiting amine or oxide treated derivative of amine of the present composition are taken in percent ratio varying from about 99:1 to about 85:15.

Furthermore, in accordance with more preferred embodiment of the present invention, the quinone methide and polymerization non-inhibiting amine or oxide treated derivative of amine of the present composition are taken in percent ratio varying from about 99:1 to about 90:10.

In accordance with even more preferred embodiment of the present invention, the quinone methide and the polymerization non-inhibiting amine or oxide treated derivative of amine of the present composition are taken in percent ratio varying from about 95:5 to about 90:10. The present composition has been, surprisingly and unexpectedly, found to give best efficiency for control and inhibition of polymerization of styrene in this range of ratio of its components.

Accordingly, in accordance with present invention, the polymerization non-inhibiting amine or oxide treated derivative of the amine is taken in an amount of equal to or less than about 50% of the total composition, and in accordance with preferred embodiment of the present invention, the polymerization non-inhibiting amine or oxide treated derivative of the amine is taken in an amount of equal to or less than about 15% of the total composition, and in accordance with more preferred embodiment of the present invention, the polymerization non-inhibiting amine or oxide treated derivative of the amine is taken in an amount of equal to or less than about 10% of the total composition, and in accordance with even more preferred embodiment of the present invention, the quinone methide and the polymerization non-inhibiting amine or oxide treated derivative of the amine are taken in percent ratio varying from about 95:5 to about 90:10.

In accordance with one of the embodiments of the present invention, the polymerization of styrene, surprisingly and unexpectedly, reduces from about 3.5% when quinone methide alone is used to about 0-1% when composition of present invention comprising quinone methide and polymerization non-inhibiting amine or oxide treated derivative of amine is used. In other words, the capability of quinone methide to control and inhibit the polymerization of styrene even at a lower dosage, surprisingly and unexpectedly, increases from about 96.5% to about 99-100% when composition of present invention comprising quinone methide and polymerization non-inhibiting amine or oxide treated derivative of the amine is used. Such substantial improvement has been achieved by composition of present invention even at a very low dosage of about 200 ppm. Considering the problems of polymerization of styrene and economics of the process, such an improvement on employing present composition is substantial improvement. The inventor has found that to reduce polymerization of styrene from about 3.5% to nil (substantially zero percent) polymerization, one will have to employ double dosage of quinone methide than the dosage of present composition. Therefore, the present composition not only reduces cost of process to inhibit polymerization of styrene, but also reduces the nitrogen concentration. These unexpected findings also confirm synergistic effect of composition of present invention comprising quinone methide and polymerization non-inhibiting amine or oxide treated derivative of the amine.

It is further surprising and unexpected that such a substantial control and inhibition of polymerization of styrene has been achieved at a very low dosage of about 200 ppm of the present composition when it comprises quinone methide and polymerization non-inhibiting amine or oxide treated derivative of the amine in the percent ratio of about 90:10.

As described herein, it is still further surprising and unexpected that when percent amount of polymerization non-inhibiting amine or oxide treated derivative of the amine of present invention is increased more than 15%, especially more than 10% of the present composition, the efficiency of present composition to control and inhibit the polymerization of styrene, surprisingly and unexpectedly, reduces, but it still remains within acceptable limits, unexpectedly in case of Quadrol it reduces to greater extent.

The present invention in addition to providing novel composition for controlling and inhibiting the polymerization of styrene to the extent of 100% also confirms that all amines do not behave in same manner, particularly when combined with quinone methide.

In one embodiment, the present invention relates to method of preparation of additive composition for control and inhibition of polymerization of styrene, wherein additive composition is prepared by mixing quinone methide and amine of the present invention, and, wherein the amine is polymerization non-inhibitor amine.

In accordance with one of the embodiments of the present invention, the said polymerization non-inhibiting amine is selected from the group comprising tri isopropanol amine (TIPA), propoxylated ethylene diamine (PED), triethanol amine (TEA), tributyl amine (TBA), diethanol amine (DEA), mono ethanol amine (MEA) and combination thereof.

In accordance with preferred embodiment of the present invention, the polymerization non-inhibiting amine is tri isopropanol amine (TIPA).

In accordance with one of the preferred embodiments of the present invention, the polymerization non-inhibiting amine is propoxylated ethylene diamine (PED).

In accordance with another preferred embodiment of the present invention, the polymerization non-inhibiting amine is tributyl amine (TBA).

In accordance with still another preferred embodiment of the present invention, the polymerization non-inhibiting amine is diethanol amine (DEA).

In accordance with yet another preferred embodiment of the present invention, the polymerization non-inhibiting amine is triethanol amine (TEA).

In accordance with further preferred embodiment of the present invention, the polymerization non-inhibiting amine is mono ethanol amine (MEA).

In accordance with one of the preferred embodiments of the present invention, the propoxylated ethylene diamine (PED) is one as available from BASF under the tradename Quadrol 204®. However, the present invention is not limited to Quadrol 204®.

The inventor has also found that when oxide treated derivative of amine is used to prepare present composition, the efficiency of the amine to inhibit the polymerization of styrene, surprisingly and unexpectedly, improves further.

Therefore, in one embodiment of the present invention, it relates to the method of preparation of additive composition for control and inhibition of polymerization of styrene comprising mixing quinone methide and oxide treated derivative of amine, wherein the amine is polymerization non-inhibitor amine.

In accordance with one of the preferred embodiments of the present invention, the oxide treated derivative of amine is selected from a group comprising ethylene oxide, propylene oxide and butylene oxide treated derivatives of amine.

In accordance with one of the preferred embodiments of the present invention, the oxide treated derivative of amine is ethoxylated (ethylene oxide treated) derivative of N,N,disec-butyl-para-phenylene diamine (UOP5+EO).

In accordance with one of the embodiments of the present invention, the quinone methide and polymerization non-inhibiting amine or oxide treated derivative of amine are mixed in percent ratio varying from about 99:1 to about 50:50.

In accordance with one of the preferred embodiments of the present invention, the quinone methide and polymerization non-inhibiting amine or oxide treated derivative of amine are mixed in percent ratio varying from about 99:1 to about 85:15.

In accordance with one of the more preferred embodiments of the present invention, the quinone methide and polymerization non-inhibiting amine or oxide treated derivative of amine are mixed in percent ratio varying from about 99:1 to about 90:10.

In accordance with one of the even more preferred embodiments of the present invention, the quinone methide and polymerization non-inhibiting amine or oxide treated derivative of amine are mixed in percent ratio varying from about 95:5 to about 90:10.

In another embodiment, the present invention relates to use of additive composition to control and inhibit polymerization of styrene, wherein additive composition comprises amine and quinone methide, and wherein the amine is polymerization non-inhibitor amine.

In accordance with one of the embodiments of the present invention, the said polymerization non-inhibiting amine is selected from the group comprising tri isopropanol amine (TIPA), propoxylated ethylene diamine (PED), triethanol amine (TEA), tributyl amine (TBA), diethanol amine (DEA), mono ethanol amine (MEA) and combination thereof.

In accordance with preferred embodiment of the present invention, the polymerization non-inhibiting amine is tri isopropanol amine (TIPA).

In accordance with one of the preferred embodiments of the present invention, the polymerization non-inhibiting amine is propoxylated ethylene diamine (PED).

In accordance with another preferred embodiment of the present invention, the polymerization non-inhibiting amine is tributyl amine (TBA).

In accordance with still another preferred embodiment of the present invention, the polymerization non-inhibiting amine is diethanol amine (DEA).

In accordance with yet another preferred embodiment of the present invention, the polymerization non-inhibiting amine is triethanol amine (TEA).

In accordance with further preferred embodiment of the present invention, the polymerization non-inhibiting amine is mono ethanol amine (MEA).

In accordance with one of the preferred embodiments of the present invention, the propoxylated ethylene diamine (PED) is one as available from BASF under the tradename Quadrol 204®. However, the present invention is not limited to Quadrol 204®.

The inventor has also found that when oxide treated derivative of amine is used in the composition of present invention to control and inhibit polymerization of styrene, the efficiency of the amine, surprisingly and unexpectedly, improves further.

Therefore, in another embodiment the present invention relates to use of additive composition to control and inhibit polymerization of styrene, wherein additive composition comprises oxide treated derivative of amine and quinone methide, wherein the amine is polymerization non-inhibitor amine.

In accordance with one of the preferred embodiments of the present invention, the oxide treated derivative of amine is selected from a group comprising ethylene oxide, propylene oxide and butylene oxide treated derivatives of amine.

In accordance with one of the preferred embodiments of the present invention, the oxide treated derivative of amine is ethoxylated (ethylene oxide treated) derivative of N,N,disec-butyl-para-phenylene diamine (UOP5+EO).

In accordance with one of the embodiments of the present invention, the quinone methide and polymerization non-inhibiting amine or oxide treated derivative of amine are used in percent ratio varying from about 99:1 to about 50:50.

In accordance with one of the preferred embodiments of the present invention, the quinone methide and polymerization non-inhibiting amine or oxide treated derivative of amine are used in percent ratio varying from about 99:1 to about 85:15.

In accordance with one of the more preferred embodiments of the present invention, the quinone methide and polymerization non-inhibiting amine or oxide treated derivative of amine are used in percent ratio varying from about 99:1 to about 90:10.

In accordance with one of the even more preferred embodiments of the present invention, the quinone methide and polymerization non-inhibiting amine or oxide treated derivative of amine are used in percent ratio varying from about 95:5 to about 90:10.

In accordance with present invention the quinone methide is 4-benzylidene,2,6-di-tert butyl cyclohexa-2,5-dienone.

In accordance with present invention, the additive compositions of present invention may be used after mixing its components, i.e. as pre-blended composition or each ingredient of the composition may be added separately to the processing unit of styrene.

Accordingly, in one embodiment, the present invention also relates to a method of using the additive compositions of present invention for control and inhibition of polymerization of styrene, wherein the method comprises adding composition consisting of mixture of quinone methide and said amine or said oxide derivative of amine in a percent ratio as described herein to the reactor of styrene polymerization.

Accordingly, in one embodiment, the present invention also relates to a method of using the additive compositions of present invention for control and inhibition of polymerization of styrene, wherein the method comprises separately adding the components a) quinone methide and b) said amine or said oxide derivative of amine of said additive composition in a percent ratio as described herein to the reactor of styrene polymerization.

It may be added continuously to satisfy requirement of continuous flow of styrene in the processing or manufacturing unit. It may be added directly to the processing unit, or after dissolving in a suitable solvent or diluent which may include aromatic solvent or diluent. It may be added either in the beginning of process or when the manufacturing process has started.

In accordance with present invention, about 1 to 1200 ppm, especially about 1 to 400 ppm, more especially about 150 to 300 ppm, specifically about 200 to 300 ppm of present composition may be added based on weight of the reacting material in polymerization of styrene.

In accordance with present invention, the additive compositions may be used or employed at a temperature range varying from about 60 to 170° C., especially from about 90 to 140° C.

It may be noted that the expression "are taken in percent ratio varying from about 99:1 to about 50:50" and so on are intended to include the ratio of 99:1 and 50:50, and so on.

It may also be noted that "in percent ratio" means "in weight percent ratio" or "in percent ratio by weight" unless specifically otherwise provided.

EXAMPLES

The present invention is now described with the help of following examples, which are not intended to limit scope of the present invention.

Experiment:

10 g distilled styrene and required amine are taken in a reactor equipped with thermometer and nitrogen inlet and outlet. Enough $N_2$ flow is maintained to ensure proper agitation. The contents of the reactor are heated to 120° C. under continuous nitrogen flow for 2 h. After 2 h, the reactor is cooled to below 10° C. by immersing in crushed ice. The contents of the reactor are then poured into a beaker containing methanol. The precipitate obtained is filtered, dried to remove methanol and weighed. Approximately, for 1.5-2 g chilled polymerization, 80 g methanol was used to precipitate the polymer formed in the styrene solution. The weight of the precipitate is reported as % polymer formed in below Tables. The styrene was purified before use to remove the stabilizers.

Examples—Blank and with Prior Art Additive—Quinone Methide

The above experiment without additive is carried out to get the blank reading.

The above experiment with prior art additive—quinone methide (4 Benzylidene, 2,6 di Tert Butyl Cyclohexa-2,5 dienone) is carried for various active dosages varying from 150 ppm to 400 ppm for comparison purpose.

TABLE 1

| Example No. | Additive | Active Dosage (ppm) | % Polymerization |
|---|---|---|---|
| 1 | Blank | — | 19.66 |
| 2a | Quinone Methide | 100 | 9.6 |
| 2b | Quinone Methide | 150 | 7.24 |
| 2c | Quinone Methide | 200 | 3.5 |
| 2d | Quinone Methide | 250 | 2.35 |
| 2e | Quinone Methide | 300 | 0.60 |
| 2f | Quinone Methide | 350 | 0.14 |
| 2g | Quinone Methide | 400 | about 0.0 |

It can be seen from the above Table 1 that prior art additive quinone methide shows best efficiency at a dosage of 400 ppm with polymerization of styrene being Nil % (substantially zero percent), and acceptable efficiency at 350 ppm with polymerization of styrene being 0.14% and 300 ppm with polymerization of styrene being 0.60%, that is polymer concentration is maintained at less than 1.0%. When the dosage of quinone methide was reduced to 250 ppm, the polymerization of styrene increased to 2.35%, and when the dosage of quinone methide was further reduced to 200 ppm, the polymerization of styrene further increased to 3.5%, and when the dosage of quinone methide was further reduced to 150 ppm, the polymerization of styrene substantially increased to 7.24%, and when the dosage of quinone methide was further reduced to 100 ppm, the polymerization of styrene substantially increased to 9.6%. Therefore, it is observed that quinone methide is not suitable at lower dosages.

Examples with Amines Per Se of Present Compositions:

The above experiment with amines per se of present invention is carried out at 200 ppm to know whether these amines per se are capable of inhibiting the polymerization of styrene or not, and data is given in Table 2.

TABLE 2

| Example No. | Additive | Active Dosage (ppm) | % Polymerization |
|---|---|---|---|
| 3 | Quadrol | 200 | 14.64 |
| 4 | TIPA [from Sterling] | 200 | 17.08 |
| 5 | TIPA [from DOW] | 200 | 16.16 |
| 6 | TEA | 200 | 16.9 |
| 7 | TBA | 200 | 16.21 |
| 8 | DEA | 200 | 15.27 |
| 9 | MEA | 200 | 15.47 |
| 10 | UOP5 | 200 | 17.80 |

It can be seen from the above Table 2 that all amines per se of present invention at a dosage of about 200 ppm result in polymerization of styrene to the extent varying from about 14.64% to 17.80%, which on comparison with data of blank experiment confirms that amines per se of present invention are not capable of inhibiting the polymerization of styrene, and therefore, the amines of present invention have been named as polymerization non-inhibitors amines.

In view of above findings, in following experiments, 100, 200 and 300 ppm, especially 200 ppm dosage of additive composition is selected to compare the efficiency of present composition vis-à-vis prior art additives.

Examples with Present Composition Vis-à-Vis Prior Art Composition:

The above experiment was carried out with compositions of present invention comprising various amines of present invention and quinone methide to know the inhibition capability of compositions of present invention and data was compared with prior art additive.

TABLE 3

| Ex. No. | Dosage in ppm (in %) ↓ | QM + Amine → | QM + TIPA | QM + Quadrol | QM + TBA | QM + DEA | QM + TEA | QM + MEA | QM + 4HT |
|---|---|---|---|---|---|---|---|---|---|
| 11. | 198 + 2 (99:1) | | 0.32 | 0.37 | 0.91 | 0.68 | 1.54 | 1.28 | 2.82 |
| 12. | 196 + 4 (98:2) | | 0.29 | 0.22 | 0.87 | 0.66 | 1.03 | 1.25 | 1.78 |
| 13. | 190 + 10 (95:5) | | 0.12 | 0.09 | 0.84 | 0.65 | 0.98 | 1.23 | 1.70 |
| 14. | 180 + 20 (90:10) | | 0.07 | 0.00 | 0.39 | 0.69 | 0.35 | 1.04 | 1.64 |
| 15. | 170 + 30 (85:15) | | 0.58 | 2.59 | 1.24 | 1.41 | 0.85 | 1.45 | 1.70 |

In above Table 3, QM is quinone methide, TIPA is tri isopropanol amine, Quadrol is propoxylated ethylene diamine available from BASF under the tradename Quadrol 204®, TBA is tributyl amine, DEA is diethanol amine, TEA is triethanol amine, MEA is mono ethanol amine, and 4HT is 4 hydroxy tempo 2,2,6,6-tetramethyl-, 1-oxide.

In above Table 3, the compositions QM+TIPA, QM+Quadrol, QM+TBA, QM+DEA, QM+TEA, QM+MEA are compositions of present invention, and composition QM+4HT is prior art composition.

It can be seen from the above Table 3 that compositions QM+TIPA and QM+Quadrol of present invention in all percent ratios at 200 ppm dosage are far superior than prior art additive quinone methide (re Table 1), amine per se (re Table 2) and prior art composition of QM and 4HT (re last column of Table 3). It can also be seen that compositions QM+TIPA and QM+Quadrol of present invention in percent ratio of 90:10 show substantially superior efficiency towards styrene polymerization inhibition at the active dosage of 200 ppm. Only about 0 to 0.07% of styrene is polymerized with 200 ppm dosage of these compositions of present invention, which is substantial improvement over prior art additives which at 200 ppm dosage of quinone methide results in about 3.5% polymerization of styrene, and of Quadrol alone results in 14.64% polymerization of styrene, and TIPA alone results in about 16.16-17.08% polymerization of styrene, and prior art composition of QM and 4HT results in about 1.64% polymerization of styrene.

It can be seen from the above Table 3 that compositions QM+TBA, QM+DEA and QM+TEA of present invention in all percent ratios at 200 ppm dosage are far superior than prior art additive quinone methide (re Table 1), amine per se (re Table 2) and prior art composition of QM and 4HT (re last column of Table 3). It can also be seen that compositions QM+TBA, QM+DEA and QM+TEA of present invention in percent ratio of 90:10 show substantially superior efficiency towards styrene polymerization inhibition at the active dosage of 200 ppm. Only about 0.39 to 0.69% of styrene is polymerized with 200 ppm dosage of these compositions of present invention, which is substantial improvement over prior art additive which at 200 ppm dosage of quinone methide results in about 3.5% polymerization of styrene, and of TBA alone results in 16.21% polymerization of styrene, and DEA alone results in about 15.27% polymerization of styrene, and TEA alone results in about 16.9% polymerization of styrene, and prior art composition of QM and 4HT which results in about 1.64% polymerization of styrene.

It can also be seen from the above Table 3 that composition QM+MEA of present invention in all percent ratios at 200 ppm dosage is far superior than prior art additive quinone methide (re Table 1), amine per se (re Table 2) and prior art composition of QM and 4HT (re last column of Table 3). It can also be seen that composition QM+MEA of present invention in percent ratio of 90:10 shows substantially superior efficiency towards styrene polymerization inhibition at the active dosage of 200 ppm. Only about 1.04% of styrene is polymerized with 200 ppm dosage of this composition of present invention, which is substantial improvement over prior art additive which at 200 ppm dosage of quinone methide results in about 3.5% polymerization of styrene, and of MEA alone results in 15.47% polymerization of styrene, and prior art composition of QM and 4HT which results in about 1.64% polymerization of styrene.

It can be seen from the above Table 3 that, surprisingly and unexpectedly, mere 1% addition of polymerization non-inhibiting amine of present invention substantially improves the polymerization inhibition efficiency of quinone methide confirming surprising effect of compositions of present invention.

The present compositions comprising QM and TIPA, and QM and TBA were also compared with compositions comprising QM and EDA (ethylene diamine), QM and TEPA (tetraethylene pentaamine), and QM and Octyl amine at 100, 200 and 300 ppm dosages, and the results are given in following Tables 4, 5 and 6.

TABLE 4

(at 100 ppm dosage)

| Ex. No. | Dosage in ppm (in %) ↓ | QM + Amine → | QM + TIPA | QM + TBA | QM + EDA | QM + TEPA | QM + Octyl Amine |
|---|---|---|---|---|---|---|---|
| 16. | 99 + 1 (99:1) | | 5.66 | 7.91 | 9.45 | 9.53 | 8.62 |
| 17. | 98 + 2 (98:2) | | 5.46 | 7.65 | 9.24 | 9.65 | 8.48 |
| 18. | 95 + 5 (95:5) | | 5.12 | 7.45 | 9.71 | 9.91 | 8.04 |
| 19. | 90 + 10 (90:10) | | 4.95 | 7.44 | 10.64 | 10.5 | 7.33 |
| 20. | 85 + 15 (85:15) | | 5.05 | 6.05 | 13.5 | 13.1 | 6.75 |
| 21. | 80 + 20 (80:20) | | 5.15 | 5.33 | 14.2 | 13.9 | 6.95 |
| 22. | 70 + 30 (70:30) | | 5.53 | 5.90 | 15.6 | 14.52 | 7.55 |
| 23. | 50 + 50 (50:50) | | 6.12 | 6.30 | 17.5 | 15.15 | 10.32 |

It can be seen from above experimental data of Table 4 that it confirms that just about 100 ppm of composition consisting of 99 to 90% QM and 1 to 10% TIPA is able to reduce polymerization from about 9.6% to about 5.66-4.95%. Similarly, just about 100 ppm of composition consisting of 99 to 90% QM and 1 to 10% TBA is able to reduce polymerization from about 9.6% to about 7.91-7.44%. However, the amines EDA, TEPA and Octyl Amine do not show similar efficiency in reducing the polymerization of styrene.

TABLE 5

(at 200 ppm dosage)

| Ex. No. | Dosage in ppm (in %) ↓ | QM + Amine → | QM + TIPA | QM + TBA | QM + EDA | QM + TEPA | QM + Octyl Amine |
|---|---|---|---|---|---|---|---|
| 24. | 198 + 2 (99:1) | | 0.32 | 0.91 | 3.40 | 3.62 | 3.25 |
| 25. | 196 + 4 (98:2) | | 0.29 | 0.87 | 3.24 | 3.65 | 3.05 |
| 26. | 190 + 10 (95:5) | | 0.12 | 0.84 | 3.14 | 3.90 | 2.95 |
| 27. | 180 + 20 (90:10) | | 0.07 | 0.39 | 2.94 | 4.86 | 2.81 |
| 28. | 170 + 30 (85:15) | | 0.58 | 1.24 | 3.16 | 6.21 | 3.23 |
| 29 | 160 + 40 (80:20) | | 0.86 | 1.38 | 4.06 | 7.06 | 3.45 |
| 30 | 140 + 60 (70:30) | | 1.55 | 1.56 | 6.91 | 7.34 | 3.52 |
| 31. | 100 + 100 (50:50) | | 1.62 | 1.74 | 9.42 | 7.93 | 4.07 |

It can be seen from above experimental data of Table 5 that it confirms that just about 200 ppm of composition consisting of 99 to 90% QM and 1 to 10% TIPA is able to substantially reduce polymerization from about 9.6% to about 0.32-0.07%. Similarly, just about 200 ppm of composition consisting of 99 to 90% QM and 1 to 10% TBA is able to substantially reduce polymerization from about 9.6% to about 0.91-0.39%. However, the amines EDA, TEPA and Octyl Amine do not show similar efficiency in reducing the polymerization.

TABLE 6

(at 300 ppm dosage)

| Ex. No. | Dosage in ppm (in %) ↓ | QM + Amine → | QM + TIPA | QM + TBA | QM + EDA | QM + TEPA | QM + Octyl Amine |
|---|---|---|---|---|---|---|---|
| 32. | 297 + 3 (99:1) | | 0.17 | 0.46 | 0.75 | 0.7 | 0.63 |
| 33. | 294 + 6 (98:2) | | 0.08 | 0.42 | 0.83 | 0.82 | 0.58 |
| 34. | 285 + 15 (95:5) | | 0.03 | 0.35 | 0.92 | 1.15 | 0.56 |
| 35. | 270 + 30 (90:10) | | 0.0 | 0.28 | 1.12 | 1.32 | 0.61 |
| 36. | 255 + 45 (85:15) | | 0.15 | 0.75 | 1.72 | 1.65 | 0.78 |
| 37. | 240 + 60 (80:20) | | 0.32 | 0.78 | 1.89 | 1.75 | 0.97 |
| 38. | 210 + 90 (70:30) | | 0.56 | 0.84 | 2.1 | 1.84 | 1.14 |
| 39. | 150 + 150 (50:50) | | 0.61 | 0.89 | 2.15 | 1.95 | 1.43 |

It can be seen from above experimental data of Table 6 that it confirms that just about 300 ppm of composition consisting of 99 to 90% QM and 1 to 10% TIPA is able to substantially reduce polymerization from about 9.6% to about 0.17-Nil % (substantially zero percent). Similarly, just about 300 ppm of composition consisting of 99 to 90% QM and 1 to 10% TBA is able to substantially reduce polymerization from about 9.6% to about 0.46-0.28%. The amines EDA, TEPA and Octyl Amine do show efficiency in reducing the polymerization at 300 ppm dosage, however, as can be seen from above Table 6, their efficiency is substantially poor when compared with TIPA and TBA of present invention.

It may be noted that in above Tables 4, 5 and 6, the efficiency of amines EDA, TEPA and Octyl Amine has been compared with 100, 200 and 300 ppm dosages of present compositions comprising QM and TIPA, and QM and TBA. However, having regard to experimental findings in above Table 3, it can be concluded that even present compositions comprising QM and Quadrol, and QM and DEA, and QM and TEA, and QM and MEA will also demonstrate similar trend in efficiency at dosages of 100 and 300 ppm as these have demonstrated at 200 ppm dosage of the composition.

It can also be seen from the above Tables 3, 4, 5 and 6 that, surprisingly and unexpectedly, when percent amount of polymerization non-inhibiting amine of present invention is increased more than 10% of the present composition, that is when 15% of polymerization non-inhibiting amine of present invention is taken the efficiency of present composition to control and inhibit the polymerization of styrene, surprisingly and unexpectedly, reduces, but it still remains within acceptable limits for all amines except for Quadrol, which is further unexpected and presently reasons could not found for this unexpected behavior of Quadrol.

At present, the inventor has not been able to assign reasons for surprising and unexpected sudden decrease in efficiency of all amines when their percentage in the composition consisting of QM and the selected amine is increased above 10%. It may be noted that decrease in efficiency of amines TIPA and TBA of present invention is very low as compared to other amines.

The above experimental findings clearly and unambiguously establish surprising and unexpected synergistic nature of present compositions.

Examples with Present Composition and Prior Art Compositions:

The above experiment was also carried out with further embodiment of present invention comprising ethoxylated derivative of amine, which is ethoxylated derivative of N,N, disec-butyl-para-phenylene diamine (UOP5+EO) and quinone methide (QM) to know the inhibition capability of composition of present invention and experimental findings were compared with UOP5, UOP5+EO (ethyloxylated derivative of UOP5), prior art compositions comprising QM and N,N,disec-butyl-para-phenylene diamine (UOP5), and comprising QM and 4HT, and results are given Table 7.

TABLE 7

| Ex. No. | Dosage in ppm (in %) ↓ | Composition → | QM + (UOP5 + EO) | QM + UOP5 | QM + 4HT |
|---|---|---|---|---|---|
| 40. | 198 + 2 (99:1) | | 1.52 | 3.32 | 2.82 |
| 41. | 196 + 4 (98:2) | | 1.23 | 3.30 | 1.78 |
| 42. | 190 + 10 (95:5) | | 0.96 | 3.10 | 1.70 |

TABLE 7-continued

| Ex. No. | Dosage in ppm (in %) ↓ | Composition → | QM + (UOP5 + EO) | QM + UOP5 | QM + 4HT |
|---|---|---|---|---|---|
| 43. | 180 + 20 (90:10) | | 0.55 | 3.51 | 1.64 |
| 44. | 170 + 30 (85:15) | | 0.81 | 4.08 | 1.70 |

It can be seen from the above Table 7 that composition QM+(UOP5+EO) of present invention in all percent ratios at 200 ppm dosage is far superior than UOP5, which results in 17.8% polymerization of styrene at 200 ppm (re Table 2); UOP5+EO, which, as found by inventor, results in 9.25% polymerization of styrene at 200 ppm (with 2.4 moles of UOP5+EO); prior art additive quinone methide (re Table 1) which results in 3.5% polymerization of styrene at 200 ppm, and prior art composition of QM+UOP5 (re second last column of Table 7) which results in about 3.10 to 3.50% polymerization of styrene, and prior art composition of QM and 4HT (re last column of Table 7) which results in about 1.64 to 2.82% polymerization of styrene.

The present composition is also far superior than UOP5+EO per se which results in 9.25% polymerization of styrene at 200 ppm.

It can also be seen from the above Table 7 that compositions QM+(UOP5+EO) of present invention in percent ratio of 90:10 show substantially superior efficiency towards styrene polymerization inhibition at the active dosage of 200 ppm. Only about 0.55% of styrene is polymerized at 200 ppm dosage of this composition of present invention, which is substantial improvement over prior art additive which at 200 ppm dosage of quinone methide results in about 3.5% polymerization of styrene, and prior art composition of QM and UOP5 which results in about 3.51% polymerization of styrene, and prior art composition of QM and 4HT which results in about 1.64% polymerization of styrene. At present, the inventor has not been able to assign reasons for surprising and unexpected sudden decrease in efficiency of above composition of present invention when their percentage in the composition consisting of QM and the selected amine is increased above 10%.

It can also be seen from the above Table 7 that, surprisingly and unexpectedly, only ethoxylated derivative of UOP5 of present invention substantially improves the polymerization inhibition efficiency of quinone methide confirming its surprising effect.

The above experimental findings clearly and unambiguously establish surprising and unexpected synergistic nature of present compositions.

The above findings also confirm that compositions of present invention have technical advantages and surprising effects over the prior art additives and compositions.

The invention claimed is:

1. Additive composition for control and inhibition of polymerization of styrene, wherein the composition consists of amine and quinone methide, and wherein said amine is selected from the group consisting of tri isopropanol amine (TIPA), propoxylated ethylene diamine (PED), triethanol amine (TEA), tributyl amine (TBA), diethanol amine (DEA), mono ethanol amine (MEA), and combination thereof.

2. The additive composition as claimed in claim 1, wherein said amine is selected from the group consisting of tri isopropanol amine (TIPA), propoxylated ethylene diamine (PED), and triethanol amine (TEA), and combination thereof.

3. The additive composition as claimed in claim 1, wherein said amine is tributyl amine (TBA).

4. The additive composition as claimed in claim 1, wherein said amine is selected from the group consisting of diethanol amine (DEA), and mono ethanol amine (MEA), and combination thereof.

5. Additive composition for control and inhibition of polymerization of styrene, wherein the composition consists of oxide treated derivative of amine and quinone methide, and wherein said oxide treated derivative of amine is selected from a group consisting of ethylene oxide, propylene oxide and butylene oxide treated derivatives of amine.

6. The additive composition as claimed in claim 5, wherein said oxide treated derivative of amine is ethoxylated derivative of N,N,disec-butyl-para-phenylene diamine.

7. The additive composition as claimed in claim 1, wherein said composition consists of quinone methide and said amine in weight percent ratio which is selected from the group consisting of the weight percent ratio varying from 99:1 to 50:50, from 99:1 to 85:15, from 99:1 to 90:10, and from 95:5 to 90:10.

8. The additive composition as claimed in claim 1, wherein said quinone methide is 4-benzylidene,2,6, di-tert butyl cyclohexa-2,5 dienone.

9. A method of preparation of additive composition for control and inhibition of polymerization of styrene, wherein the method comprises mixing quinone methide and amine, wherein said amine is selected from the group consisting of tri isopropanol amine (TIPA), propoxylated ethylene diamine (PED), triethanol amine (TEA), tributyl amine (TBA), diethanol amine (DEA), mono ethanol amine (MEA), and combination thereof; and wherein said quinone methide and said amine are mixed in a weight percent ratio selected from the group consisting of the weight percent ratio varying from 99:1 to 50:50, from 99:1 to 85:15, from 99:1 to 90:10, and from 95:5 to 90:10.

10. A method of using the additive composition of claim 1 for control and inhibition of polymerization of styrene, wherein the method comprises adding composition consisting of mixture of quinone methide and said amine in a weight percent ratio selected from the group consisting of the weight percent ratio varying from 99:1 to 50:50, from 99:1 to 85:15, from 99:1 to 90:10, and from 95:5 to 90:10 to reactor of styrene polymerization.

11. A method of using the additive composition of claim 1 for control and inhibition of polymerization of styrene, wherein the method comprises separately adding components a) quinone methide and b) said amine of said additive composition in a weight percent ratio selected from the group consisting of the weight percent ratio varying from 99:1 to 50:50, from 99:1 to 85:15, from 99:1 to 90:10, and from 95:5 to 90:10 to the reactor of styrene polymerization.

12. The method as claimed in claim 10, wherein said composition is used in an amount which is selected from the group consisting of the amount varying from 1 to 1200 ppm, from 1 to 400 ppm, from 150 to 300 ppm, and from 200 to 300 ppm of based on weight of the reacting material in polymerization of styrene.

13. The method as claimed in claim 10, wherein said composition is used at a temperature range which is selected from the group consisting of the temperature varying from 60 to 170° C., and from 90 to 140° C.

14. The additive composition as claimed in claim 5, wherein said composition consists of quinone methide and said oxide treated derivative of amine in weight percent ratio which is selected from the group consisting of the weight percent ratio varying from 99:1 to 50:50, from 99:1 to 85:15, from 99:1 to 90:10, and from 95:5 to 90:10.

15. The additive composition as claimed in claim 5, wherein said quinone methide is 4-benzylidene,2,6, di-tert butyl cyclohexa-2,5 dienone.

16. A method of preparation of additive composition for control and inhibition of polymerization of styrene, wherein the method comprises mixing quinone methide and oxide treated derivative of amine, wherein said oxide treated derivative of amine is selected from a group consisting of ethylene oxide, propylene oxide and butylene oxide treated derivatives of amine, and wherein said quinone methide and said oxide treated derivative of amine are mixed in a weight percent ratio selected from the group consisting of the weight percent ratio varying from 99:1 to 50:50, from 99:1 to 85:15, from 99:1 to 90:10, and from 95:5 to 90:10.

17. The method as claimed in claim 16, wherein said oxide treated derivative of amine is ethoxylated derivative of N,N, disec-butyl-para-phenylene diamine.

18. A method of using the additive composition of claim 5 for control and inhibition of polymerization of styrene, wherein the method comprises adding composition consisting of mixture of quinone methide and said oxide treated derivative of amine in a weight percent ratio selected from the group consisting of the weight percent ratio varying from 99:1 to 50:50, from 99:1 to 85:15, from 99:1 to 90:10, and from 95:5 to 90:10 to reactor of styrene polymerization.

19. The method of using the additive composition of claim 5 for control and inhibition of polymerization of styrene, wherein the method comprises separately adding components a) quinone methide and b) said oxide derivative of amine of said additive composition in a weight percent ratio selected from the group consisting of the weight percent ratio varying from 99:1 to 50:50, from 99:1 to 85:15, from 99:1 to 90:10, and from 95:5 to 90:10 to the reactor of styrene polymerization.

20. The method as claimed in claim 11, wherein said composition is used in an amount which is selected from the group consisting of the amount varying from 1 to 1200 ppm, from 1 to 400 ppm, from 150 to 300 ppm, and from 200 to 300 ppm of based on weight of the reacting material in polymerization of styrene.

21. The method as claimed in claim 11, wherein said composition is used at a temperature range which is selected from the group consisting of the temperature varying from 60 to 170° C., and from 90 to 140° C.

22. The method as claimed in claim 18, wherein said composition is used in an amount which is selected from the group consisting of the amount varying from 1 to 1200 ppm, from 1 to 400 ppm, from 150 to 300 ppm, and from 200 to 300 ppm of based on weight of the reacting material in polymerization of styrene.

23. The method as claimed in claim 18, wherein said composition is used at a temperature range which is selected from the group consisting of the temperature varying from 60 to 170° C., and from 90 to 140° C.

24. The method as claimed in claim 19, wherein said composition is used in an amount which is selected from the group consisting of the amount varying from 1 to 1200 ppm, from 1 to 400 ppm, from 150 to 300 ppm, and from 200 to 300 ppm of based on weight of the reacting material in polymerization of styrene.

25. The method as claimed in claim 19, wherein said composition is used at a temperature range which is selected from the group consisting of the temperature varying from 60 to 170° C., and from 90 to 140° C.

* * * * *